US006756411B2

(12) United States Patent
Betts et al.

(10) Patent No.: US 6,756,411 B2
(45) Date of Patent: Jun. 29, 2004

(54) PROCESS FOR PRODUCING OXYGENATED PRODUCTS

(75) Inventors: Mark Justin Betts, Vereeniging (ZA); Mark Eberhard Dry, Cape Town (ZA); Arie Geertsema, Sasolburg (ZA); Gerhardus Johannes Hendricus Rall, Varderbijlpark (ZA)

(73) Assignee: Sasol Technology (Proprietary) Limited, Johannesburg (ZA)

( * ) Notice: Subject to any disclaimer, the term of this patent is extended or adjusted under 35 U.S.C. 154(b) by 21 days.

(21) Appl. No.: 10/281,909

(22) Filed: Oct. 28, 2002

(65) Prior Publication Data

US 2003/0120118 A1 Jun. 26, 2003

Related U.S. Application Data

(63) Continuation of application No. 08/981,567, filed as application No. PCT/GB96/01563 on Jun. 28, 1996.

(30) Foreign Application Priority Data

Jun. 28, 1996 (ZA) .............................................. 95/5405

(51) Int. Cl.⁷ ......................... C07C 27/00; C07C 45/00; C07C 27/20
(52) U.S. Cl. ....................... 518/701; 518/700; 518/706; 518/715; 568/451; 568/909
(58) Field of Search ................................ 518/700, 706, 518/715, 701; 568/451, 909

(56) References Cited

U.S. PATENT DOCUMENTS

| | | | |
|---|---|---|---|
| 3,239,566 A | 3/1966 | Slaugh et al. ................ 260/604 |
| 3,239,569 A | 3/1966 | Slaugh et al. ................ 260/632 |
| 3,239,570 A | 3/1966 | Slaugh et al. ................ 260/632 |
| 3,239,571 A | 3/1966 | Slaugh et al. ................ 260/632 |
| 3,369,050 A | 2/1968 | Greene ........................ 260/632 |
| 3,420,898 A | 1/1969 | Van Winkle et al. ........ 260/632 |
| 3,440,291 A | 4/1969 | Van Winkle et al. ........ 260/632 |
| 3,448,157 A | 6/1969 | Slaugh et al. ................ 260/604 |
| 3,448,158 A | 6/1969 | Slaugh et al. ................ 260/604 |
| 3,527,809 A | 9/1970 | Pruett et al. ................. 260/604 |
| 3,527,818 A | 9/1970 | Mason et al. ................ 260/632 |
| 3,737,475 A | 6/1973 | Mason .................... 260/683.15 |
| 3,875,204 A | 4/1975 | Ghirga et al. ............. 260/465.3 |
| 4,179,403 A | 12/1979 | Kim et al. ................... 252/431 |
| 4,198,352 A | 4/1980 | Kim et al. ................... 260/604 |
| 4,330,678 A | 5/1982 | Van Leeuwen et al. ..... 568/454 |
| 4,408,078 A | 10/1983 | Van Leeuwen et al. ..... 568/454 |
| 4,414,421 A | 11/1983 | Drent ......................... 568/462 |
| 4,443,638 A | 4/1984 | Yates ......................... 568/882 |
| 4,467,116 A | 8/1984 | Van Leeuwen et al. ..... 568/454 |
| 4,537,997 A | 8/1985 | Kojima et al. ............... 568/454 |
| 4,577,986 A | 3/1986 | Sie .............................. 585/324 |
| 4,578,523 A | 3/1986 | Bahrmann et al. .......... 568/454 |
| 4,590,311 A | 5/1986 | Drent ......................... 568/852 |
| 4,680,168 A | 7/1987 | Goodall et al. ............... 423/22 |
| 4,723,047 A | 2/1988 | Bahrmann et al. .......... 568/862 |
| 4,731,487 A | 3/1988 | Drent ......................... 568/454 |
| 4,806,693 A | 2/1989 | Drent ......................... 568/417 |
| 4,851,582 A | 7/1989 | Drent ......................... 568/387 |
| 5,072,057 A | 12/1991 | Oswald et al. ............... 568/840 |
| 5,189,003 A | 2/1993 | Klusener et al. ............ 502/167 |
| 5,210,280 A | 5/1993 | Drent ......................... 560/204 |
| 5,214,220 A | 5/1993 | Drent ......................... 568/881 |
| 5,227,532 A | 7/1993 | Sato et al. ................... 568/454 |
| 5,256,827 A | 10/1993 | Slaugh et al. ................ 568/454 |
| 5,258,524 A | 11/1993 | Quan et al. ............... 548/335.1 |
| 5,258,546 A | 11/1993 | Klusener et al. ............ 560/207 |
| 5,304,686 A | 4/1994 | Slaugh et al. ................ 568/496 |
| 5,304,691 A | 4/1994 | Arhancet et al. ........... 568/867 |
| 5,498,801 A | 3/1996 | Chaudhari et al. .......... 568/454 |

FOREIGN PATENT DOCUMENTS

| | | |
|---|---|---|
| CA | 2111026 | 6/1994 |
| EP | 0005569 | 11/1979 |
| EP | 0024761 | 3/1981 |
| EP | 0033554 | 8/1981 |
| EP | 0163234 | 5/1985 |
| EP | 0309056 | 9/1988 |
| EP | 0423874 | 4/1991 |
| EP | 0478850 | 4/1992 |
| EP | 0495548 | 7/1992 |
| EP | 0499328 | 8/1992 |
| GB | 1254063 | 11/1971 |
| GB | 1338237 | 11/1973 |
| GB | 1540227 | 2/1979 |
| GB | 1555551 | 11/1979 |
| GB | 1561273 | 2/1980 |
| GB | 2075857 | 11/1981 |
| GB | 2217318 | 10/1989 |
| GB | 2256641 | 12/1992 |
| GB | 2261662 | 5/1993 |
| GB | 2274457 | 7/1994 |
| WO | 9420510 | 9/1994 |
| ZA | 939292 | 12/1993 |

OTHER PUBLICATIONS

Dry, M. E. "The Fischer–Tropsch Synthesis." Catalysis Science & Technology, vol. 1 (1979) pp. 159–255.
Gerhartz, W. et al. "Chlorophenols to Copper Compounds." Ullmann's Encyclopedia of Industrial Chemistry, vol. A7, (1986) pp. 206–216.
Mark, H. F. et al. "Oxo Process." Kirk–Othmer Encyclopedia of Chemical Technology, Third Edition, vol. 16 (1989) pp. 637–653.
Cornils, B. et al. "Oxo with Rhodium Catalysts." Hydrocarbon Processing (Jun. 1975) pp. 83–91.
Lemke, H. "Select Best Oxo Catalyst Cycle." Hydrocarbon Processing, vol. 45, No. 2 (Feb. 1966) pp.148–152.

Primary Examiner—J. Parsa
(74) Attorney, Agent, or Firm—Ladas & Parry

(57) ABSTRACT

A process for producing oxygenated products from an olefin-rich feedstock comprise reacting, in a hydroformylation stage, a Fischer-Tropsch derived olefinic product comprising linear and methyl branched olefins, with carbon monoxide and hydrogen in the presence of a catalytically effective quantity of a hydroforhylation catalyst and under hydroformylation reaction conditions, to produce oxygenated products comprising linear and methyl branched aldehydes and/or alcohols. The Fischer-Tropsch derived olefinic product is that obtained by subjecting a synthesis gas comprising carbon monoxide (CO) and hydrogen ($H_2$) to Fischer-Tropsch reaction conditions in the presence of a Fischer-Tropsch catalyst.

30 Claims, 3 Drawing Sheets

PROCESS FOR PRODUCING OXYGENATED PRODUCTS

This application is a continuation of Ser. No. 08/981,567 filed Mar. 4, 1998 which is a 371 of PCT/GB96/01563 filed Jun. 28, 1996.

This invention relates to a process for producing oxygenated products. More particularly, it relates to a process for producing oxygenated products from an olefin-rich feedstock. Still more particularly, the invention relates to a process for producing oxygenated products such as aldehydes and/or alcohols from an olefin-rich feedstock by means of hydroformylation.

According to a first aspect of the invention, there is provided a process for producing oxygenated products from an olefin-rich feedstock, which process comprises reacting, in a hydroformylation stage, a Fischer-Tropsch derived olefinic product obtained by subjecting a synthesis gas comprising carbon monoxide (CO) and hydrogen ($H_2$) to Fischer-Tropsch reaction conditions in the presence of an iron-based, a cobalt-based or an iron/cobalt-based Fischer-Tropsch catalyst, with carbon monoxide and hydrogen in the presence of a catalytically effective quantity of a hydroformylation catalyst and under hydroformylation reaction conditions, to produce oxygenated products comprising aldehydes and/or alcohols.

The process of the first aspect of the invention is thus characterized thereby that it utilizes said Fischer-Tropsch derived olefinic product as feedstock for the hydroformylation stage. This feedstock is thus obtained by subjecting a synthesis gas comprising carbon monoxide and hydrogen to Fischer-Tropsch reaction conditions in the presence of an iron-based or a cobalt-based Fischer-Tropsch catalyst.

Thus, according to a second aspect of the invention, there is provided a process for producing oxygenated products, which process comprises subjecting, in a Fischer-Tropsch reaction stage, a synthesis gas comprising carbon monoxide (CO) and hydrogen ($H_2$) to Fischer-Tropsch reaction conditions in the presence of an iron-based, a cobalt-based or an iron/cobalt-based Fischer-Tropsch catalyst, to obtain an olefinic product;

optionally, working up the olefinic product to remove unwanted components therefrom and/or to separate a particular olefinic component therefrom; and feeding the olefinic product or the olefinic component as a feedstock to a hydroformylation stage in which the feedstock is reacted with carbon monoxide and hydrogen in the presence of a catalytically effective quantity of a hydroformylation catalyst and under hydroformylation reaction conditions, to produce oxygenated products comprising aldehydes and/or alcohols.

More particularly, the Fischer-Tropsch catalyst and reaction conditions may be selected to give an olefinic product having desired characteristics, depending on the particular oxygenated products required from the hydroformylation stage Thus, for example, the catalyst and reaction conditions may be those utilized in fluidized bed reactors or reaction stages, eg those commonly known as Synthol reactors, or those utilized in fixed bed reactors or reaction stages, or those utilized in slurry bed reactors or reaction stages, as hereinafter described.

The predominant Fischer-Tropsch products from, for example, Synthol reactors, can be olefins. These are predominantly linear and mono-methyl α-olefins, with lesser quantities of linear and mono-methyl branched internal olefins. The balance of the Fischer-Tropsch products comprise aromatics, paraffins and oxygenates such as ketones, aldehydes, alcohols, and carboxylic acids. Typically, in the olefinic product, more than one mono-methyl α-olefin isomer is present for any given carbon number, with the methyl group being present at any position along the α-olefin molecule backbone or linear hydrocarbon chain.

A high degree of olefin feedstock purity and linearity have hitherto been regarded as essential for effective hydroformylation thereof; in contrast, in the present invention, it was unexpectedly found that a Fischer-Tropsch derived olefinic product, containing large amounts or proportions of additional, ie non-olefinic, components with different functional groups, as well as relatively large amounts of non-linear or branched olefins, can be used, directly or indirectly, as a hydroformylation feedstock, The Fischer-Tropsch stage olefinic product or the olefinic component as hereinbefore described can thus be used directly in the hydroformylation stage without any substantial purification or further processing thereof to remove unwanted components such as non-olefins. The non-olefinic components in single or multiple carbon number fractions of the Fischer-Tropsch stage product then act as a reaction medium and/or a solvent medium in the hydroformylation stage, and can thus have a beneficial effect in the hydroformylation stage. These non-olefinic components can ultimately be separated from the heavier hydroformylation stage products, eg by means of distillation, and used as synthetic fuels or the like. It is believed that the additional cost of processing such inert components in the hydroformylation stage is more than compensated for by the saving realized in not having to separate them from the hydroformylation stage feedstock. This is especially true for the higher olefin containing Fischer-Tropsch material, in which it may be difficult to purify and/or separate the valuable olefins from the balance of the Fischer-Tropsch products having structures and boiling points similar to the required olefins. Subjecting such material to hydroformylation conditions favouring the formation of linear products, results in selective 'removal' of the olefins by their reacting to form heavier and still more valuable aldehydes and/or alcohols which in turn may be easily separated on the basis of temperature. This simplifies the beneficiation of the olefins. However, if present, organic acids should be removed as these can be deleterious to hydroformylation.

However, the process of the invention also envisages that the olefinic product from the Fischer-Tropsch reaction stage can, if desired, be worked up to remove unwanted components therefrom and/or to separate a particular olefinic component therefrom, in which case this component can be used as the feedstock to the hydroformylation stage. This working up typically involves distillation, and may include conventional, vacuum, extractive or reactive distillation. Instead, or additionally, the working up may involve techniques such as membrane separation. The olefin content and distribution of the feedstock to the hydroformylation stage can thus be tailored according to the oxygenated products which are required. Thus, a discrete or multiple carbon number olefin product from the Fischer-Tropsch stage may thus be processed further to produce narrower 'cuts' in which linear α-olefins are concentrated; when such cuts are used as hydrotormylation stage feedstock, hydroformylation products with increased linearity are obtained.

While the Fischer-Tropsch reaction stage and the hydroformylation stage can be separated from each other so that the olefinic product from the Fischer-Tropsch reaction stage can be stored or transported independently of the hydroformylation stage, the Applicant envisages that the stages will preferably be integrated so that the olefinic product from the Fischer-Tropsch stage passes directly to the hydroformylation stage with at most the working up of the olefin product and possibly some intermediate storage thereof between the stages taking place.

In the light of this integration, the carbon monoxide and hydrogen required for the hydroformylation can typically be in the form of synthesis gas, which can then be the same as that used in the Fischer-Tropscsh stage. This has the added advantage that all the reactants in the hydroformylation stage are then essentially sulphur free since the synthesis gas is sulphur free.

If alcohols are the desired hydroformylation product, then the overall $H_2$:CO usage ratios for the Fischer-Tropsch reaction and hydroformylation stages may be approximately equal, thereby more readily facilitating integration of the gas systems of these stages.

The hydroformylation stage feedstock is thus, depending on the Fischer-Tropsch reaction conditions and product workup, free of sulphur and typically contains between 35% and 100% by mass olefins. Of the total olefin content of the feedstock, between 50% and 100% by. mass may be linear α-olefins, between 0% and 60% mono-methyl branched α-olefins, and between 0% and 10% linear internal olefins.

The Fischer-Tropsch reaction may be effected in a fixed bed, in a slurry bed, or, preferably, in a fluidized bed reactor. The Fischer-Tropsch reaction conditions may include utilizing a reaction temperature of between 190° C. and 340° C., with the actual reaction temperature being largely determined by the reactor configuration. Thus, when a fluidized bed reactor is used, the reaction temperature is preferably between 300° C. and 340° C.; when a fixed bed reactor is used, the reaction temperature is preferably between 200° C. and 250° C.; and when a slurry bed reactor is used, the reaction temperature is preferably between 190° C. and 270° C., An inlet synthesis gas pressure to the Fischer-Tropsch reactor of between 1 and 50 bar, preferably between 15 and 50 bar, may be used. The synthesis gas may have a $H_2$:CO molar ratio, in the fresh feed, of 1,5:1 to 2,5:1, preferably 1,8:1 to 2,2:1. A gas recycle may optionally be employed in the reactor, and the ratio of the gas recycle rate to the fresh feed rate, on a molar basis, may then be between 1:1 and 3:1, preferably between 1,5:1 and 2,5:1. A space velocity, in $m^3$ (kg catalyst)$^{-1}$ hour$^{-1}$, of from 1 to 20, preferably from 8 to 12, may be utilized in the reactor.

In principle, an iron-based, a cobalt-based or an iron/cobalt-based Fischer-Tropsch catalyst can be used in the Fischer-Tropsch reaction stage; however, an iron-based catalyst is preferred.

The iron-based Fischer-Tropsch catalyst may comprise iron and/or iron oxides which have been precipitated or fused. However, iron and/or iron oxides which have been sintered, cemented, or impregnated onto a suitable support can also be used. The iron should be reduced to metallic Fe before the Fischer-Tropsch synthesis. The iron based catalyst may contain various levels of promoters, the role of which may be to alter one or more of the activity, the stability, and the selectivity of the final catalyst. Preferred promoters are those influencing the surface area of the reduced iron ('structural promoters'), and these include oxides or metals of Mn, Ti, Mg, Cr, Ca, Si, Al, or Cu or combinations thereof. Preferred promoters for influencing product selectivities are alkali oxides of K and Na. The alkali oxide to structural promoter mass ratio may be between 0:1 and 20:1 but should preferably be between 0,1:1 and 2:1. The structural promoter content thereof, expressed as grams of structural promoter per 100 grams Fe, may be between 0 and 50 but is preferably between 0,1 and 2 for high temperature Fischer-Tropsch applications, and between 10 and 40 for low temperature Fischer-Tropsch applications.

When the Fischer-Tropsch olefinic product is obtained in a high temperature reaction stage or reactor, such as in the synthol reactor or reaction stage, which uses a fluidized beds the iron-based Fischer-Tropsch catalyst will normally be a fused catalyst, eg that, derived by the fusion of magnetite with various levels of oxide promoters as hereinbefore described. The fused material may then be crushed or atomized to yield particles preferably having a size $\leq 70\,\mu m$, and may be reduced with $H_2$ prior to Fischer-Tropsch synthesis.

However, when the Fischer-Tropsch olefinic product is obtained in a fixed bed or a slurry bed using lower temperatures as hereinbefore described, the catalyst will normally be a precipitated or supported catalyst.

The Fischer-Tropsch catalyst may be prepared in accordance with the methods described in the article by M. E. Dry in "Catalysis Science and Technology" (1979) Volume 1; pages 159–255, Eds J. R. Anderson and M. Boudart. This article is hence incorporated herein by reference.

When a cobalt-based catalyst is used, it may comprise cobalt and/or a cobalt oxide which has been precipitated, cemented or impregnated onto a suitable support, such that the catalyst has the following composition:

1–50 g cobalt per 100 g support, preferably 5–30 g cobalt;
0–20 g promoter per 100 g support, preferably 0–10 g promoter.

Preferred supports for the cobalt-based catalyst are oxides of Ti, Mn, Si, Al or combinations thereof, while preferred promoters, when present, are metals and/or oxides of Pt, Ru, Zr, Re or combinations thereof.

The hydroformylation catalyst will thus be selected according to the particular oxygenated products required. In the case of a Synthol derived product, comprising linear α-olefins as hereinbefore described, being used as the hydroformylation stage feedstock, predominantly linear oxygenated products will be required. Thus, the hydroformylation catalyst may then be a phosphine and/or phosphite ligand modified rhodium (Rh), cobalt (Co) or ruthenium (Au) homogeneous catalyst. Such catalysts are described in, for example, U.S. Pat. Nos. 3,239,566, 3,239,570, 3,448,157, 3,448,158 and 3,527,809, which are hence incorporated herein by reference. Preferred catalysts are tri-aryl phosphorous derivatives used as ligands with rhodium, and alkyl phosphorous derivatives used as ligands with cobalt. Examples of such catalysts are tri-phenyl phosphine ligands used with rhodium, and alkyl phosphines used with cobalt. Specific examples of the latter are tri-alkyl phosphines as described in U.S. Pat. Nos. 3,239,569 and 3,239,571; 9-phosphabicyclo [4,2,1] nonane and 9-phosphabicyclo [3,3,1] nonane as described in UK Patent No. 1254063 and U.S. Pat. Nos. 3,440,291, 3,527,818 and 3,400,163; and derivatives thereof, as described in U.S. Pat. No. 3,420,898. These patents are hence also incorporated herein by reference. Derivatives and modifications of these catalysts such as heterogeneous, supported, water soluble and/or bimetallic systems, can also be used.

A rhodium, cobalt or ruthenium metal precursor and the phosphorous derivatives are usually introduced separately in the appropriate process stage, with the catalyst then forming in situ. For homogeneous phosphine modified rhodium catalysts or catalyst systems, the form of the rhodium precursor is important, while this effect is not as apparent in phosphine modified cobalt catalysts or catalyst systems.

Preferred rhodium precursors include $HCORh(P(C_6H_5)_3)_3$ and $[Rh(OOCCH_3)_2]_2$.

For ligand modified cobalt catalysts, typical hydroformylation temperatures are between 140° C. and 210° C., and preferably between 160° C. and 200° C.; synthesis gas ('syngas') composition with respect to the $H_2$:CO ratio may be 1:2–3:1, and preferably about 2:1; syngas pressure may typically be 20–110 bar, and preferably 50–90 bar, the molar ratio of ligand to metal may typically be 10:1–1:1, and preferably is 1:1–3:1; and the % metal to olefin by mass may typically be 0,01–1, and preferably is 0,2–0,7.

For cobalt hydrocarbonyl catalysts, typical hydroformylation temperatures are between 80° C. and 200° C., and preferably between 110° C. and 180° C.; syngas composition with respect to the $H_2$:CO ratio may be 1:2–2:1, and preferably about 1:1; syngas pressure may typically be 170–300 bar, and preferably 200–220 bar; and % metal to olefin by mass may typically be 0,1–1, and preferably 0,1–0,3.

For ligand modified rhodium catalysts, typical hydroformylation temperatures are between 50° C. and 150° C., and preferably between 80° C. and 130° C.; syngas composition with respect to the $H_2$:CO ratio may be 1:2–3:1, and preferably 1:1–1:2; syngas pressure may typically be between 2 and 60 bar, and preferably between 5 and 30 bar; and % metal to olefin by mass may typically be 0,001–0,1, preferably 0,01–0,05.

The hydroformylation stage products, ie the oxygenated products, can be worked up and purified by means of recognized procedures such as catalyst separation, distillations for separation of light and heavier ends from the desired products, hydrolysis of by-products by washing with caustic, and hydrogenation of aldehydes to produce alcohols, if desired.

The hydroformylation stage products are thus typically, depending on the hydroformylation stage feedstock, to a substantial extent primary alcohols and/or aldehydes. For example, if the hydroformylation stage feedstock predominantly comprises $C_{10}$ olefins, the hydroformylation stage products may comprise between 35% and 90% by mass primary linear alcohols and/or aldehydes, depending on the exact feedstock composition and the hydroformylation conditions. The balance of the alcohols and/or aldehydes would then typically comprise 60% to 9% by mass primary monomethyl alcohols and 0% to 30% primary dimethyl alcohols.

The oxygenated products of the process are characterized thereby that, generally, they are biodegradable.

The invention extends also to oxygenated products when produced by the processes of the invention. In particular, it extends to mono-methyl and/or dimethyl linear alcohols and/or aldehydes when produced by the processes of the invention, and/or to derivatives of such products, such as alcohol ethoxylates, alcohol ether sulphonates, alcohol sulphates, alkyl glycerol ether sulphonates, alkyl poly glucosides, fatty alkanolamides, α-sulphomethyl esters, fatty acids, fatty esters and phthalates.

The invention will now be described by way of the following non-limiting examples, and with reference to the following drawings.

Figure 1:
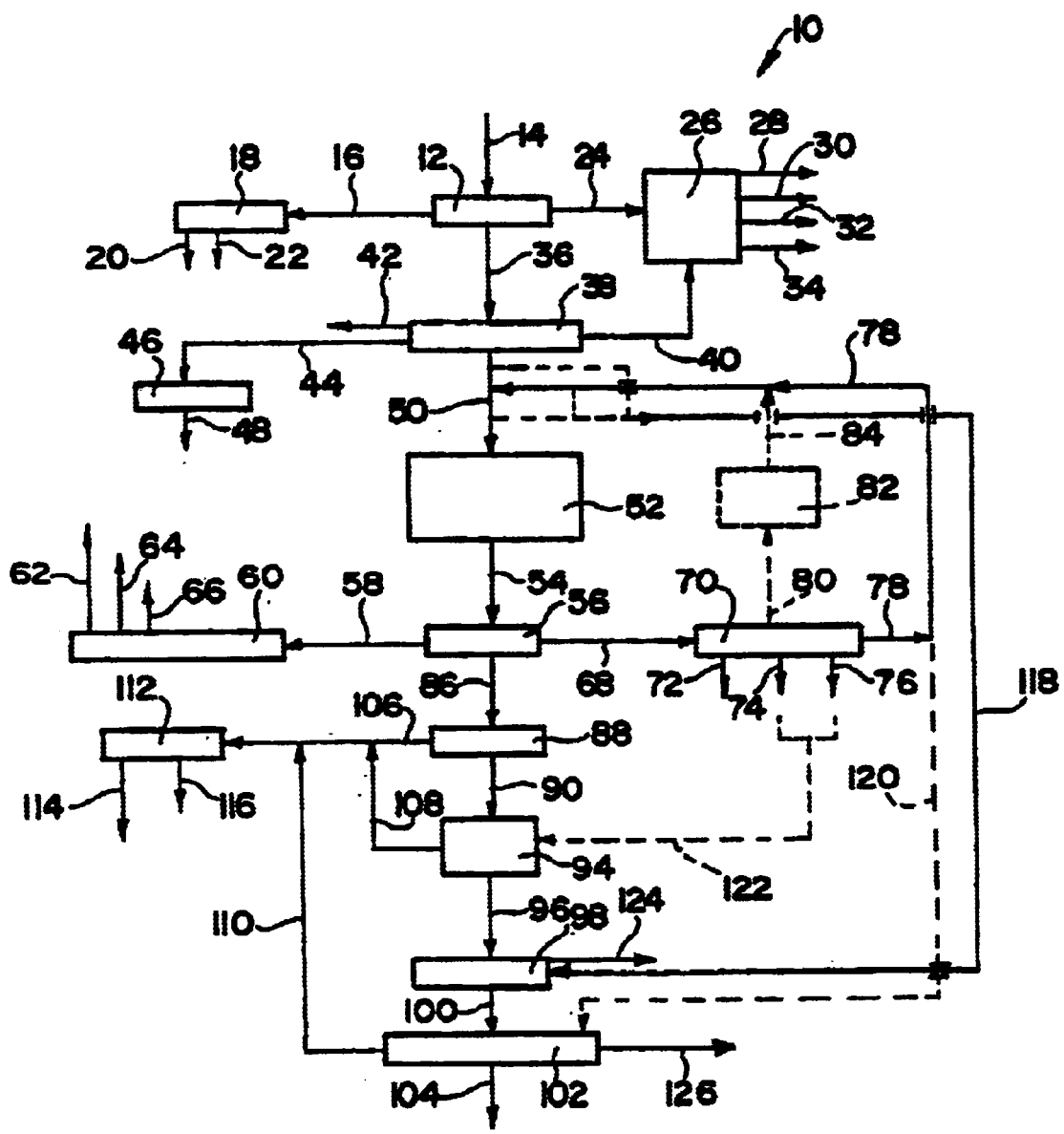
FIG. 1 shows a flow diagram of a process according to one embodiment of the invention, for producing oxygenated products.

Referring to FIG. 1, reference numeral 10 generally indicates a process according to one embodiment of the invention, for producing oxygenated products.

The process 10 includes a separation stage 12, with a raw synthesis gas flow line 14, from a coal gasification stage (not shown) leading into the separation stage 12. An aqueous fraction withdrawal line 16 leads from the stage 12 to an extraction stage 18, with a phenol withdrawal line 20 as well as an ammonia withdrawal line 22 leading from the stage 18. A heavy component withdrawal line 24 leads from the separation stage 12 to a tar and oil workup stage 26, with gasoline, diesel, bitumen and creosote withdrawal lines, designated 28, 30, 32 and 34 respectively, leading from the stage 26.

A synthesis gas Withdrawal line 36 leads from the separation stage 12 to a sulphur removal stage 38. A naphtha withdrawal line 40 leads from the stage 38 to the tar and oil workup removal stage 26. A carbon dioxide withdrawal line 42 also leads from the stage 38, as does a sulphur compound withdrawal line 44. The line 44 leads to a sulphur recovery stage 46 with a sulphur withdrawal line 48 leading from the stage 46.

A synthesis gas flow line 50 leads from the sulphur removal stage 38, to a reactor stage 52. A product line 54 leads from the reactor stage 52 to a separation stage 56. The stage 52 can use fluidized bed Synthol reactors; however, instead, slurry bed or fixed bed reactors can be used.

An aqueous fraction withdrawal line 58 leads from the stage 56 to an oxygenate workup stage 60, with ketone, alcohol and acid withdrawal lines 62, 64 and 66 respectively leading from the stage 60.

A gas phase or fraction withdrawal line 68 also leads from the stage 56 to a gas separation stage 70. Carbon dioxide, $C_2$ and $C_{3+}$ withdrawal lines, designated 72, 74 and 76 respectively, lead from the gas separation stage 70, as does a hydrogen withdrawal line 78. The line 78 leads back to the flow line 50. Optionally, a methane withdrawal line 80 can also lead from the separation stage 70 to a methane reformer 82, with a product line 84 then leading from the reformer 82 to the line 78.

An oil phase withdrawal line 86 leads from the separation stage 56 to a further separation stage 88. A product flow line 90 leads from the stage 88 to a hydroformylation feed workup stage 94, with a hydroformylation feed line 96 leading from the stage 94 to a hydroformylation stage 98. A flow line 100 leads from the stage 98 to a hydroformylation product workup stage 102 with a alcohol/aldehyde withdrawal line 104 leading from the stage 102. An off-gas withdrawal line 124 leads from the stage 98, while a heavy ends withdrawal line 126 leads from the stage 102.

An oil phase withdrawal line 106 leads from the separation stage 88, with oil phase product lines 10B and 110 leading from the stages 94, 102 respectively into the line 106. The line 106 leads to an oil workup stage 112, with a diesel withdrawal line 114 and a gasoline withdrawal line 116 leading from the stage 112.

A flow line 118 leads into the stage 98. The flow line 118 leads from the flow line 50 and/or from the flow line 78, as indicated in broken line.

If desired, a flow line 120 can lead from the flow line 78 to the stage 102.

In use, raw synthesis gas derived from the coal gasification stage is cooled in the separation stage 12, and an aqueous fraction removed therefrom. The aqueous fraction is withdrawn along the flow line 16, while heavier tar oils, which are removed along the flow line 24. The aqueous fraction and the heavier tar oil fraction can be processed further respectively in the stages 18 and 26 to yield, in the case of the water fraction, phenols and ammonia, and in the case of the tar oils, creosote and heavy tar. Upon further working of the latter, BTX (benzene, toluene, xylene mix), gasoline and diesel can be produced.

The synthesis gas then passes to the sulphur removal stage 38 where sulphur removal is effected by means of cooling and methanol washing. This firstly removes naphtha, which is withdrawn along the flow line 40 to the stage 26, and then sulphur containing gases as well as $Co_2$, which are removed along the flow lines 44, 42 respectively.

Purified synthesis gas then passes to the reactor stage 52 which comprises Fischer-Tropsch reactors containing an iron-based, cobalt-based or iron/cobalt-based catalyst. The products from the stage 52 are cooled in the separation stage 56 to remove, by condensation, oil, water and water soluble products from the reactor outlet gases. The gas fraction is withdrawn along the flow line 68, and light hydrocarbons, methane, hydrogen and carbon dioxide are separated in the separation stage 70. The methane may, optionally, be reformed in the reformer 82 into synthesis gas before being recycled to the stage 52, The aqueous fraction separated out in the separation stage 56 is withdrawn along the flow line 58 and, in the oxygenate workup stage 60, ketones, alcohols and acids are recovered therefrom.

The oil stream passes to the separation stage 88 where it is subjected to distillation to obtain hydrocarbon fractions having a carbon number distribution desirable for hydroformylation. The balance of the hydrocarbons have synthetic fuel value, and pass, along the flow line 106, to the oil workup stage 112. The oil workup stage 112 can, naturally, be the oil workup stage 26, ie separate oil workup stages need not be utilized.

The selected hydroformylation feed traction then passes to the workup stage 94. It is to be appreciated that the stage 94 is optional, and it is not essential that the selected hydroformylation feed fraction be subjected to further working up. When the workup stage 94 is present, an optional $C_2$ fraction or $C_{3+}$ fraction flow line 122 may lead from the flow lines 74, 76 to the stage 94. Instead, the flow line 122 can then lead to the stage 98, if desired (not shown). Whether or not further workup is required, depends on the specific olefin content and the distribution required and may, for example, involve caustic treatment to remove organic acids if present. Lighter olefin containing tractions from the gas separation stage 70 thus can also optionally be used as a hydroformylation feedstock by passing into the stage 94 along the flow line 118 and the flow line 122 (not shown).

The hydroformylation feed fraction then passes, along the flow line 96, into the hydroformylation stage 98. This stage comprises a hydroformylation reactor system incorporating catalyst recovery and/or catalyst recycle. Synthesis gas required for the stage 98, and comprising carbon monoxide and hydrogen, may be obtained from any suitable gas stream entering the stage 52, or being recycled thereto. However, preferably, product from the methane reformer 82 may be used as synthesis gas in the stage 98, this product thus entering along the flow line 118. This has the benefit that it comprises product which is passed over the Fischer-Tropsch catalyst in the stage 52. The Fischer-Tropsch catalyst has a high sulphur affinity and is poisoned by sulphur, and thus the synthesis gas contains very little sulphur. Off-gas from the stage 98 is withdrawn along the flow line 124, and may be used as fuel gas or may be recycled.

The product from the stage 98 passes to the workup stage 102 which includes separation of the 'inert' Fischer-Tropsch component which functions as a solvent, hydroformylation products, and heavy ends. The heavy ends are withdrawn along flow line 126 and may be beneficiated or used as fuel. The Fischer-Tropsch component with alternative synthesis fuel value is routed, along the flow line 110, to the oil workup stage 112. If alcohols are the desired product, then the workup stage 102 may involve a hydrogenation step in order to convert remaining aldehydes to alcohols.

Figure 2:
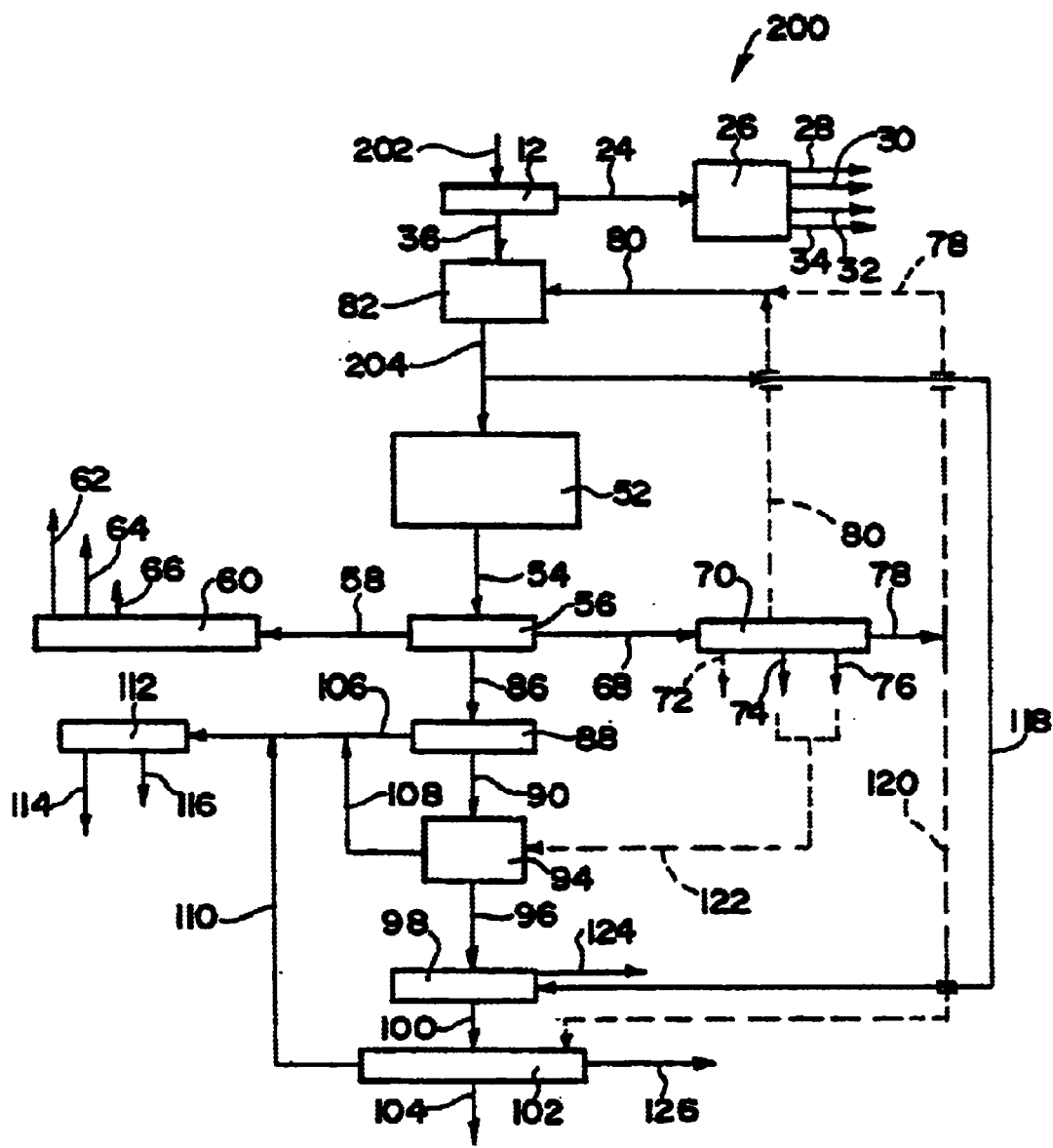
FIG. 2 shows a flow diagram of a process according to another embodiment of the invention, for producing oxygenated products.

Referring to FIG. 2, reference numeral 200 generally indicates a process according to a second embodiment of the invention for producing oxygenated products. Parts of the process 200 which are the same or similar to those of the process 10 hereinbefore described with reference to FIG. 1, are indicated with the same reference numerals.

In the process 200, a methane or natural gas flow line 202 leads into the separation stage 12, with the flow line 36 from the stage 12 leading to the methane reformer 82. A product withdrawal line 204 leads from the reformer 62 to the reactor stage 52.

The remainder of the process 200 is substantially the same as the process 10, and it functions in substantially identical fashion to the process 10.

EXAMPLE 1

In a simulation of the Fischer-Tropsch reactor stage 52 of the processes 10, 200, an olofinic product, suitable for use as a feedstock for a subsequent hydroformylation stage in accordance with the invention, was prepared by passing synthesis gas, in a fluidized bed pilot plant scale reactor, over a fused iron catalyst. The catalyst contained, as a chemical promoter, potassium oxide ($k_2O$) and, as structural promoter, silica ($SiO_2$), such that the $K_2O/SiO_2$ molar ratio was approximately 0,5 and the mass of $K_2O$ used was approximately 0,5 g/100 g of Fe. The mass of catalyst load expressed in kg fe was 4,2 and the catalyst bed height was 2 meters.

The reactor temperature and pressure were maintained at ±320° C. and ±23 bar respectively. The molar ratio of $H_2$:CO in the fresh synthesis gas was approximately 2:1 with a recycle rate to fresh feed rate ratio of approximately 2:1. A total gas linear velocity of 45 cm $sec^{-1}$ was used. Under these conditions, the CO and $H_2$ conversion was ±93%. The selectivity to the $C_{5-18}$ oil fraction based on carbon atom % was ±42%. This fraction was separated from the balance of the products using condensation in a simulation of the stage 56. The oil fraction was distilled, in a simulation stage 94, using conventional or vacuum distillation procedures to yield various olefinic containing fractions, hereinafter referred to as Fischer-Tropsch fractions. Various of these fractions were pretreated and subjected to hydroformylation as described in the following examples.

EXAMPLE 2

A $C_1$ Fischer-Tropsch fraction in accordance with Example 1, was subjected to azeotropic distillation with methanol. The overhead fraction comprising a $C_3$ Fischer-Tropsch derived component and methanol, was subjected to hydroformylation. The pretreatment of the feedstock in this manner resulted in the removal of the oxygenates originating from the Fischer-Tropsch reaction. The Fischer-Tropsch component of this hydroformylation feedstock comprised ±81% by mass 1-octene, while the feedstock comprised ±67% by mass methanol. 150 ml of the feedstock was loaded into an autoclave together with a rhodium catalyst precursor [Rh) $OOCCH_3)_2]_2$, and triphenylphosphine ($P(C_6H_5)_3$) as liganding agent, such that the % Rh/olefin by mass was ±0,08 and the $P(C_6H_5)_3$:Rh ratio by moles was 100:1. The material was subjected to hydroformylation for 5 hours at a constant temperature of 90° C. and an initial pressure of 25 $bar_g$ using syngas, ie synthesis gas, with a molar $H_2$:CO ratio of 2:1. Gas chromatography (GC) analysis of the reaction products indicated an α-olefin conversion of ±96% and a selectivity to $C_9$ aldehydes of ±100% based on the number of moles of olefin converted. Of the aldehyde products, ±81% were linear, the balance being mono-methyl branched.

EXAMPLE 3

A $C_9$ Fischer-Tropsch fraction in accordance with Example 1 was distilled, and a $C_9$ Fischer-Tropsch material recovered as an overhead product. This material war used as a hydroformylation feedstock in this Example. The Fischer-Tropsch component of the feedstock comprised ±62% by mass 1-nonene, and ±18% by mass iso-nonenes comprising various mono-methyl branched α-olefins. The balance of the Fischer-Tropsch component consisted of various paraffins, aromatics and oxygenates having boiling points similar to the relevant $C_9$ olefins. 150 ml of the feedstock was loaded into an autoclave together with 50 ml n-octane, a rhodium catalyst precursor $[Rh(OOCCH_3)_2]_2$ and tri-phenylphosphine $(P(C_6H_5)_3)$ as liganding agent, such that the % Rh/olefin by mass was ±0,04 and the $P(C_6H_5)_3$:Rh ratio by moles was 100:1. The material was subjected to hydroformylation for 4 hours at a constant temperature of 90° C. and an initial pressure of 25 $bar_g$ using syngas with a molar $H_2$:CO ratio of 2:1. GC analysis of the reaction products indicated an α-olefin conversion of ±94% and selectivities to $C_{10}$ aldehydes and $C_9$ paraffins of ±99% and ±1% respectively, based on the number of moles of olefin converted. Of the aldehyde products, 81% were linear, the balance being mono-methyl branched.

EXAMPLE 4

A $C_{10}$ Fischer-Tropsch fraction in accordance with Example 1 was distilled, and a $C_{10}$ Fischer-Tropsch material recovered as an overhead product. This material was used as a hydroformylation feedstock in this example. The Fischer-Tropsch component of the feedstock comprised ±63% by mass 1-decene, and ±5% by mass iso-decenes comprising various mono-methyl branched α-olefins. The balance of the Fischer-Tropsch component consisted of various paraffins, aromatics and oxygenates having boiling points similar to the relevant $C_{10}$ olefins. 150 ml of the material was loaded into an autoclave together with 50 ml n-octane, a rhodium catalyst precursor $[Rh(OOCCH_3)_2]_2$ and tri-phenylphosphine $(P(C_6H_5)_3)$ as liganding agent, such that the % Rh/olefin by mass was ±0,04 and the $P(C_6H_5)_3$:Rh ratio by moles was 100:1. The material was subjected to hydroformylation for 10 hours at a constant temperature of 90° C. and an initial pressure of 25 $bar_g$ using syngas with a molar $H_2$:CO ratio of 2:1. GC analysis of the reactor products indicated an α-olefin conversion of 96% and selectivities to $C_{11}$ aldehydes and $C_{10}$ paraffins of ±84% and ±13% respectively, based on the number of moles of olefin converted. Of the hydroformylation products, 84% were linear with the balance being mainly mono-methyl aldehydes and alcohols.

EXAMPLE 5

A $C_9$ Fischer-Tropsch material having the same composition as that of Example 3, was used as hydroformylation feedstock in this example. 150 ml of this material was loaded into an autoclave together with 50 ml n-octane, a cobalt catalyst precursor $Co(OOCCH_3)_2.4H_2O$ and tri-n-butylphosphine $(P(C_4H_9)_3)$ as liganding agent, such that the % Co/olefin by mass was ±0,5 and the $P(C_4H_9)_3$:Co ratio by moles was 5:1. The Material was subjected to hydroformylation at a constant temperature of 150° C. and an initial pressure of 70 $bar_g$ using syngas with a molar $H_2$:Co ratio of 2:1. After 3 hours, GC analysis undertaken on the reactor products indicated an α-olefin conversion of ±68% and selectivities to $C_{10}$ aldehydes, $C_{10}$ alcohols $C_9$ paraffins, $C_9$ internal olefins and heavier oxygenated products of ±2%, ±64%, ±9%, ±18% and ±6% respectively, based on the moles of α-olefin converted. Of the hydroformylation products, ±84% were linear, with balance being mainly mono-mathyl alcohols.

EXAMPLE 6

A $C_{10}$ Fischer-Tropsch fraction in accordance with Example 1 was fractionated and redistilled, and a $C_{10}$ Fischer-Tropsch material recovered as an overhead product. This material was used as a hydroformylation feedstock. The feedstock comprised ±80% olefins by mass of which ±75% were linear α-olefins, ±15% were mono-methyl α-olefins and ±10% were linear internal olefins. The balance of the feedstock consisted of various,paraffins, aromatics and oxygenates having boiling points similar to the relevant $C_{10}$ olefins. 100 ml of this material was loaded into an autoclave together with a Co precursor $Co(OOCCH_3)_2.4H_2O$, and tri-n-octylphosphine $(P(C_8H_{17})_3)$ as liganding agent, such that the % Co/olefin by mass was ±0,5 and the $P(C_8H_{17})_3$:Co ratio by moles was 2:1. The material was subjected to hydroformylation at a constant temperature of 170° C. and a constant pressure of 70 $bar_g$ using syngas with a $H_2$:CO ratio of 2:1. After 8 hours, GC analysis of the reactor products indicated an α-olefin conversion of ±93% and selectivities to $C_{11}$ aldehydes, $C_{11}$ alcohols, $C_{10}$ paraffins, and heavier oxygenated products of ±0,5%, ±86%, ±11% and ±2,5% respectively, based on the moles of α-olefin converted. Of the hydroformylation products, ±67% by mass were linear with the balance being mainly mono-methyl alcohols.

EXAMPLE 7

A $C_{10}$ Fischer-Tropsch fraction in accordance with Example 1 was distilled, and the overhead product thereof treated with aqueous NaOH. The resultant $C_{10}$ Fischer-Tropsch material was used as hydroformylation feedstock in this example. The feedstock comprised ±53% olefins by mass, of which ±69% were linear α-olefins, ±27% were mono-methyl α-olefins and ±4% were linear internal olefins. The balance of the feedstock consisted of paraffins, aromatics and oxygenates all having boiling points similar to the relevant $C_{10}$ olefins. 100 ml of the feedstock was loaded into an autoclave together with a Co precursor $Co(OOCCH_3)_2.4H_2O$, and tri-n-octylphosphine $(P(C_8H_{17})_3)$ as liganding agent, such that the % Co/olefin by mass was ±0,5 and the $P(C_8H_{17})_3$:Co ratio by moles was 2:1. The material was subjected to hydroformylation at a constant temperature of 170° C. and a constant pressure of 70 bar, using syngas with a $H_2$:CO ratio of 2:1. After 8 hours, GC analysis of the reactor products indicated an overall olefin conversion of ±90% and selectivities to $C_{11}$ aldehydes, $C_{11}$ alcohols, $C_{10}$ paraffins, and heavier oxygenated products of ±1%, ±88%, ±10% and ±1% respectively, based on the moles of olefin converted. Of the hydroformylation products, ±66% were linear with the balance being mainly mono-methyl alcohols.

EXAMPLE 8

A $C_{10}$ Fischer-Tropsch fraction in accordance with Example 1 was used as a hydroformylation feedstock. The feedstock comprised ±57% olefins by mass, of which ±65% were linear and ±35% were mono-methyl α-olefins. The balance of the feedstock consisted of paraffins, aromatics and oxygenates all having boiling points similar to the relevant $C_{10}$ olefins. 100 ml of the feedstock was loaded into an autoclave together with the precursor $Co(OOCCH_3)_2 \cdot 4H_2O$ and ti-n-butylphomphine ($P(C_4H_9)_3$) as liganding agent, such that the Co concentration was 0,1258 g/100 ml and the $(P(C_4H_9)_3)$:Co molar ratio was 5:1. The material was subjected to hydroformylation at a constant temperature of 200° C. and an initial pressure of 100 bar(g), using syngas with a $H_2$:CO ratio of 2:1. After 3,7 hours, GC analysis of the reactor products indicated an α-olefin conversion of 93% and selectivities to $C_{11}$ aldehydes, $C_{11}$ alcohols, $C_{10}$ paraffins, internal olefins and heavier oxygenated products of ±5% ±78%, ±8%, ±5% and ±5% respectively, based on the moles of α-olefins converted. Of the hydroformylation products ±50% were linear with the balance consisting mainly of mono-methyl alcohols and aldehydes.

EXAMPLE 9

For purposes of comparison, a mixture of pure 1-decene and n-octane was used as a hydroformylation feedstock. The feedstock comprised ±50% olefins by mass, of which ±100% were linear. The balance of the feedstock consisted of n-octane which was used to "simulate" the balance of the Fischer-Tropsch components in Example 8. 100 ml of the feedstock was loaded into an autoclave together with the precursor $Co(OOCCH_3)_2 \cdot 4H_2O$ and tri-n-butylphosphine ($P(C_4H_9)_3$) as liganding agent, such that the Co concentration was 0,1739 g/100 ml and the $(P(C_4H_9)_3)$: Co molar ratio was 5:1. The material was subjected to hydroformylation at a constant temperature of 200° C. and an initial pressure of 100 bar(g) using syngas with a $H_2$:CO ratio of 2:1. After 3,7 hours, GC analysis of the reactor products indicated an α-olefin conversion of 100% and selectivities to $C_{11}$ aldehydes, $C_{11}$ alcohols, $C_{10}$ paraffins, internal olefins and heavier oxygenated products of ±3%, ±71%, ±21%, ±0% and ±5% respectively, based on the moles of α-olefins converted. Of the hydroformylation products ±79% were linear with the balance consisting of 2-methyl and other branched $C_{11}$ alcohols and aldehydes derived from hydroformylation of internal olefins.

On comparison of the alcohol products obtained in Examples 8 and 9, it is evident that internal olefins in the Fischer-Tropsch products are less susceptible to direct hydroformylation compared with a pure linear α-olefin feed. This has an effect on the branched product composition in the hydroformylation product spectrum. Branched alcohols derived from internal olefins (in pure linear feeds) have longer branched chains, compared with branched alcohols derived from Synthol feeds which were of the methyl variety.

EXAMPLE 10

A $C_{11-12}$ Fischer-Tropsch fraction in accordance with Example 1 was distilled, and the overhead product thereof treated with aqueous NaOH. The resultant $C_{11-12}$ Fischer-Tropsch material was used as hydroformylation feedstock in this example. The feedstock comprised ±50% $C_{11}$ and $C_{12}$ olefins by mass, of which ±59% were linear α-olefins, ±37% were mono-methyl α-olefins and ±4% were linear internal olefins. The balance of the feedstock consisted of paraffins, aromatics and oxygenates all having boiling points similar to the relevant $C_{11}$ and $C_{12}$ olefins. 100 ml of the feedstock was loaded into an autoclave together with Co-octanoate as a Co precursor, and 9-eicosyl-9-phosphabicyclononane ($CH_3(CH_2)_{19}$—$P(C_8H_{16})$) as liganding agent, such that the % Co/olefin by mass was ±0,38 and, the P:Co ratio by moles was 2:1. The material was subjected to hydrotormylation at a constant temperature of 170° C. and a constant pressure of 70 $bar_g$ using syngas with a molar $H_2$:CO ratio of 2:1. After 8 hours, GC analysis of the reactor products indicated an overall olefin conversion of ±99% and selectivities to $C_{12+13}$ aldehydes, $C_{12+13}$ alcohols, $C_{11+12}$ paraffins, and heavier oxygenated products of ±3%, ±93%, ±4% and ±>1% respectively, based on the moles of olefin converted. Of the hydroformylation products, ±50% were linear with the balance consisting mainly of mono-methyl alcohols.

EXAMPLE 11

Figure 3:
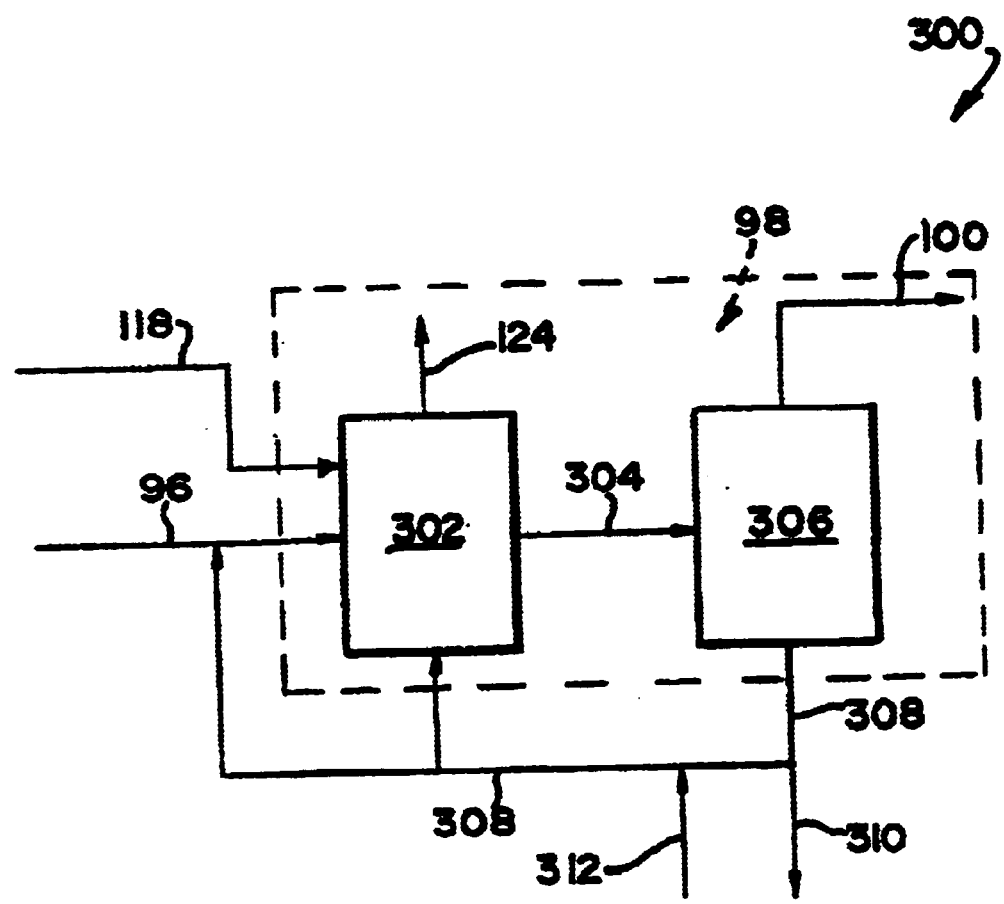
FIG. 3 shows a flow diagram of a process according to yet another embodiment of the invention, for producing oxygenated products.

In order to demonstrate further the suitability of synthol products as a hydroformylation feedstock, a $C_{11-12}$ Fischer-Tropsch fraction in accordance with Example 10, was tested in a continuously operated reactor system, as shown in FIG. 3. The reaction conditions employed were similar to those given in Example 10.

In FIG. 3, reference numeral 300 thus generally indicates a process according to another embodiment of the invention, for producing oxygenated products.

Parts of the process 300 which are the same or similar to those of the processes 10, 200, are indicated with the same reference numerals, and some parts of the process 300, which are the same as those of the processes 10, 200, have been omitted.

The process 300 thus, in essence, comprises a different hydrotormylation or oxo stage 98, to the processes 10, 200. The stage 98 of the process 300 comprises at least one hydroformylation reactor 302, with the flow lines 96, 116 leading into the reactor 302. The flow line 124 leads from the reactor 302. A product flow line 304 leads from the reactor 302 to a distillation stage 306.

The distillate or product withdrawal line 100 for withdrawing alcohols, aldehydas, converted olefins and synthol 'inerts', leads from the stage 306. A heavier products withdrawal line 308 also lead& from the stage 306, as a recycle line back to the line 96 and/or to the reactor 302, with a purge line 310 leading from the line 308. A catalyst make-up line 312 leads into the recycle line 308. Thus, the recycle line 308 is used to recycle catalyst, heavy oxygenates and the balance of the alcohols and aldehydes, back to the reactor 302.

Use is thus made, in the stage 98 of the process 300, of distillation in the distillation stage 306 as a means of separating the catalyst from the reactor products. Preferably, falling film distillation, typically wiped film distillation, is used in the stage 306. The catalyst in a residue leg of the stags or unit 306 is recycled to the reactor 302. This is facilitated in a solution of heavy oxygenates and the balance of the hydroformylation products not recovered as distillate in the stage 306. Catalyst deactivation was not observed.

Stable operation of the continuous reactor was achieved over a time period of 60 days. The total conversion, which was limited by the size of the experimental equipment (long residence times could not be employed) was maintained at ±80% for 60 days. A change in feed necessitated that the run be terminated. Hydroformylation product selectivities and linearities were similar to those of Example 10. These values remained constant with time on stream, thereby indicating the absence of poisons in the feed.

EXAMPLE 12

To demonstrate the biodegradability of the alcohols produced by the process of the invention, $C_{11}$ alcohols obtained in similar fashion to Example 6 were further tested. The final primary alcohols contained ±40% linear 1-undecanol ±36% mono-methyl $C_{11}$, alcohols and ±24% di-methyl $C_{11}$ alcohols. Standard OECD (European Community Council Directive) procedures for biodegradability testing (OECD Council Directive: Guidelines for testing of Chemicals, Test 302A) employing a continuous 'bio-reactor' containing micro-organisms were used to test the breakdown of the abovementioned alcohols. A hydraulic retention time of ±6 hours and an alcohol concentration of ±50 ppm in water fed to the reactor were employed. Comparisons of the chemical oxygen Demand (COD) in the reactor inlet and outlet taken over a period of 30 days, indicated that ±94% of the carbon fed to the reactor was biodegraded.

EXAMPLE 13

The biodegradability of surfactants derived from products produced in accordance with the process of the invention, was tested by preparing $C_{10}$ alcohol rulphates from $C_{10}$ primary alcohol products obtained in similar fashion to Example 4 using a standard sulphation technique. Of the alcohol sulphates prepared, ±73% were linear and ±27% were composed of various mono-methyl derivatives. Subjecting this material to the same biodegradability testing procedures and conditions described in Example 12, resulted in ±99% of the carbon feed material being biodegraded.

It is thus apparent that, in the process of the invention, various Fischer-Tropsch products are suitable as hydroformylation feedstocks, giving rise to linear as well as other unique plasticizer and detergent alcohol precursors.

In accordance with the invention, the unique character of the olefin composition and distribution in the high temperature Fischer-Tropsch fractions can thus be exploited in n-alkyl phosphine modified Co catalyst systems. These catalyst systems facilitate isomerization of α-olefins to internal olefins. The internal olefins readily 're-isomerize' back to α-olefins before being hydroformylated to yield predominantly linear products. On comparing products derived from pure feeds with those derived from Synthol products, as in Example 1, it is evident that more internal olefins undergo hydroformylation in pure feeds.

The process according to the invention also has the following advantages:

- synthesis gas is the only raw material required for producing higher aldehydes and alcohols.
- the synthesis gas as well as the feedstock for the hydroformylation stage is essentially sulphur-free.
- it was unexpectedly found that unique hydroformylation products are obtained, based thereon that the Fischer-Tropsch derived feedstock to the hydroformylation stage contain linear olefins and mono-methyl α-olefins, with the methyl groups being located at any position along the α-olefin molecules linear backbone. In contrast, when using conventional linear olefin feedstocks for hydroformylation, the only mono-methyl hydroformylation products which can form are of the 2-methyl variety.
- the Fischer-Tropsch reaction products and the hydroformylation product distributions can be tailored to give desired hydroformylation product combinations.
- it was also unexpectedly found that the balance of the components in the Fisher-Tropsch products, and which comprises aromatics, oxygenates and paraffins, does not adversely effect hydrotormylation reactions, and in some cases can be beneficial; eg it can act as a polar solvent to improve the CO and $H_2$ solubility, thereby improving gas to liquid mass transfer; it can improve reaction selectivity control by varying the concentration of the reactants, intermediates and final products; and it can improve process control by acting as an additional coolant.
- the relatively high α-olefin content of the Fischer-Tropsch reaction products, and the fact that the Fischer-Tropsch components are relatively inert, means that little or no additional chemical purification or chemical workup is required as compared to known hydroformylation processes.
- the inert Fischer-Tropsch components present in the feedstock to the hydroformylation stage has alternative synthetic fuel value, and can, if desired, be hydrogenated in a hydroformylation process.
- the hydrotormylation products obtained, and derivatives thereof, are biodegradable.
- hydroformylation of the olefins in the Fischer-Tropsch fractions is an efficient way of both separating them from other Fischer-Tropsch components, which may otherwise be difficult, whilst at the same time converting them to a still more valuable product.
- the higher and lower molecular weight alcohol products obtained by the process are suitable for use as precursors for the production of biodegradable surfactants and plasticizers.

What is claimed is:

1. A process for producing oxygenated products from an olefin-rich feedstock, which process comprises reacting, in a hydroformylation stage, a substantially unpurified Fischer-Tropsch derived olefinic product comprising linear olefins, branched olefins and non-olefins, obtained by subjecting a synthesis gas comprising carbon monoxide (CO) and hydrogen ($H_2$) to Fischer-Tropsch reaction conditions, in the presence of a suitable Fischer-Tropsch catalyst to obtain said Fischer-Tropsch derived olefinic product, with carbon monoxide and hydrogen in the presence of a catalytically effective quantity of a hydroformylation catalyst and under hydroformylation reaction conditions, to produce oxygenated products comprising aldehydes and/or alcohols.

2. A process for producing oxygenated products, which process comprises:

subjecting, in a Fischer-Tropsch reaction stage, a synthesis gas comprising carbon monoxide (CO) and hydrogen ($H_2$) to Fischer-Tropsch reaction conditions, in the presence of a suitable Fischer-Tropsch catalyst, in a fluidized catalyst bed, to obtain a Fischer-Tropsch derived olefinic product comprising linear olefins, branched olefins and non-olefins;

feeding the substantially unpurified Fischer-Tropsch derived olefinic product as a feedstock to a hydroformylation stage in which the feedstock is reacted with synthesis gas in the presence of a catalytically effective quantity of a hydroformylation catalyst and under hydroformylation reaction conditions, to produce oxygenated products comprising aldehydes and/or alcohols.

3. A process according to claim 2, wherein the Fischer-Tropsch catalyst is iron-based, and comprises iron and/or iron oxides which have been precipitated, fused, or impregnated on a carrier/support.

4. A process according to claim 3, wherein the Fischer-Tropsch reaction stage comprises a fluidized bed reactor, and wherein the Fischer-Tropsch reaction conditions include a reaction temperature of between 300° C. and 340° C.

5. A process according to claim 4, wherein the Fischer-Tropsch catalyst is that derived from the fusion of magnetite with an oxide or a metal of Mn, Ti, Mg, Cr, Ca, Si, Al or Cu or combinations thereof, as structural promoter, and an alkali oxide as a promoter for influencing product selectivities.

6. A process according to claim 5 wherein, in the Fischer-Tropsch catalyst, the alkali oxide to structural promoter mass ratio is between 0:1 and 20:1, and wherein the structural promoter content thereof expressed as grams of structural promoter per 100 grams Fe, is between 0,1 and 2.

7. A process according to claim 2, wherein the linear olefins comprise linear α-olefins, while the branched olefins comprise methyl branched α-olefins in which the methyl groups are located at any position along the α-olefins' linear backbones, with the substantially unpurified Fischer-Tropsch derived olefinic product comprising at least 5% by mass of the methyl branched α-olefins, the hydroformylation stage feedstock thus including non-olefinic components with different functional groups and with the oxygenated products comprising primary linear and methyl branched aldehydes and/or primary linear and methyl branched alcohols.

8. A process according to claim 2, wherein the Fischer-Tropsch reaction stage and the hydroformylation stage are integrated so that the olefinic product from the Fischer-Tropsch stage passes directly to the hydroformylation stage with at most intermediate storage thereof between the stages taking place.

9. A process according to claim 8, wherein the synthesis gas which is used in the hydroformylation stage is the same as that used in the Fischer-Tropsch reaction stage.

10. A process for producing oxygenated products, which process comprises:

subjecting, in a Fischer-Tropsch reaction stage, a synthesis gas comprising carbon monoxide (CO) and hydrogen ($H_2$) to Fischer-Tropsch reaction conditions, in the presence of an iron-based Fischer-Tropsch catalyst, in a fluidized catalyst bed, to obtain a Fischer-Tropsch derived olefinic product comprising linear olefins, branched olefins and non-olefins;

without working up the olefinic product to remove unwanted components therefrom, feeding the olefinic product as a feedstock to a hydroformylation stage in which the feedstock is reacted with carbon monoxide and hydrogen in the presence of a catalytically effective quantity of a hydroformylation catalyst and under reaction conditions, to produce oxygenated products comprising aldehydes and/or alcohols, with non-olefinic components present in single or multiple carbon number fractions in the Fischer-Tropsch derived olefinic product, then acting as a reaction medium and/or a solvent medium in the hydroformylation stage.

11. A process according to claim 10, wherein the Fischer-Tropsch reaction stage comprises a slurry bed reactor, and wherein the Fischer-Tropsch reaction conditions include a reaction temperature of between 190° C. and 270° C.

12. A process according to claim 10, wherein the Fischer-Tropsch reaction stage comprises a fixed bed reactor, and wherein the Fischer-Tropsch reaction conditions include a reaction temperature of between 200° C. and 250° C.

13. A process according to claim 11 or claim 12, wherein the Fischer-Tropsch catalyst includes an oxide or a metal of Mn, Ti, Mg, Cr, Ca, Si, Al or Cu or combinations thereof, as a structural promoter, and an alkali oxide as a promoter for influencing product selectivities.

14. A process according to claim 13, wherein, in the Fischer-Tropsch catalyst, the alkali oxide to structural promoter mass ratio is between 0:1 and 20:1.

15. A process according to claim 10, wherein the Fischer-Tropsch catalyst is cobalt-based, and comprises cobalt and/or a cobalt oxide which has been precipitated, sintered or impregnated onto a support.

16. A process according to claim 15, wherein the cobalt-based catalyst comprises an oxide of Ti, Mn, Si, Al or combinations thereof as the support, and a metal and/or an oxide of Pt, Ru, Zr, Re or combinations thereof, as a promoter.

17. A process according to claim 15, wherein the cobalt catalyst has the following composition:

5–30 g cobalt per 100 g of support; and

0–10 g promoter per 100 g of support.

18. A process according to claim 10, wherein the Fischer-Tropsch reaction stage and the hydroformylation stage are integrated so that the olefinic product from the Fischer-Tropsch stage passes directly to the hydroformylation stage with at most intermediate storage thereof between the stages taking place.

19. A process according to claim 18, wherein the carbon monoxide and hydrogen required for the hydroformylation are in the form of sulphur-free synthesis gas, which is the same as that used in the Fischer-Tropsch stage.

20. A process according to claim 2, wherein the Fischer-Tropsch reaction conditions include an inlet synthesis gas pressure to the reaction stage of between 1 and 50 bar, and a $H_2$:CO molar ratio of 1,5:1 to 2,5:1 in respect of the synthesis gas.

21. A process according to claim 20, wherein a gas recycle to the reaction stage is optionally employed with the ratio of the gas recycle rate to the fresh synthesis gas feed rate, on a molar basis, being between 1:1 and 3:1, and wherein a space velocity, in $m^3$ (kg catalyst)$^{-1}$ hour$^{-1}$, of from 1 to 20 is used in the reaction stage.

22. A process according to claim 1, wherein the hydroformylation catalyst is a phosphine and/or phosphite ligand modified rhodium (Rh), cobalt (Co) or ruthenium (Ru) homogeneous catalyst.

23. A process according to claim 22, wherein the hydroformylation catalyst is a tri-aryl phosphorous derivative used as a ligated with rhodium, or an alkyl phosphorous derivative used as a ligand with cobalt.

24. A process according to claim 23, which includes introducing a rhodium, cobalt or ruthenium metal precursor and the phosphorous derivative separately into the hydroformylation process stage, with the catalyst then forming in situ.

25. A process according to claim 1, wherein the linear olefins comprise linear α-olefins, while the branched olefins comprise methyl branched α-olefins in which the methyl groups are located at any position along the α-olefins' linear backbones, with the substantially unpurified Fischer-Tropsch derived olefinic product comprising at least 5% by mass of the methyl branched α-olefins, and with the oxygenated products comprising primary linear and methyl branched aldehydes and/or primary linear and methyl branched alcohols.

26. A process according to claim 10, wherein the linear olefins comprise linear α-olefins, while the branched olefins comprise methyl branched α-olefins in which the methyl groups are located at any position along the α-olefins' linear backbones, with the substantially unpurified Fischer-Tropsch derived olefinic product comprising at least 5% by mass of the methyl branched α-olefins, and with the oxygenated products comprising primary linear and methyl branched aldehydes and/or primary linear and methyl branched alcohols.

27. A process according to claim 2, wherein the hydroformylation catalyst is a phosphine and/or phosphite ligand modified rhodium (Rh), cobalt (Co) or ruthenium (Ru) homogeneous catalyst.

28. A process according to claim 10, wherein the hydroformylation catalyst is a phosphine and/or phosphite ligand modified rhodium (Rh), cobalt (Co) or ruthenium (Ru) homogeneous catalyst.

29. A process for producing oxygenated products from an olefin-rich feedstock, which process comprises reacting, in a hydroformylation stage, a substantially unpurified Fischer-Tropsch derived olefinic product comprising linear olefins, branched olefins and non-olefins, obtained by subjecting a synthesis gas comprising carbon monoxide (CO) and hydrogen ($H_2$) to Fischer-Tropsch reaction conditions, in the presence of a suitable Fischer-Tropsch catalyst to obtain said Fischer-Tropsch derived olefinic product, with carbon monoxide and hydrogen in the presence of a catalytically effective quantity of a phosphine and/or phosphite ligand modified rhodium (Rh), cobalt (Co) or ruthenium (Ru) homogeneous catalyst and under hydroformylation reaction conditions, to produce oxygenated products comprising aldehydes and/or alcohols.

30. A process for producing a biodegradable surfactant precursor, which process comprises:

reacting, in a hydroformylation stage, a substantially unpurified Fischer-Tropsch derived olefinic product comprising linear olefins, branched olefins and non-olefins, obtained by subjecting a synthesis gas comprising carbon monoxide (CO) and hydrogen ($H_2$) to Fischer-Tropsch reaction conditions, in the presence of a suitable Fischer-Tropsch catalyst to obtain said Fischer-Tropsch derived olefinic product, with carbon monoxide and hydrogen in the presence of a catalytically effective quantity of a hydroformylation catalyst and under hydroformylation reaction conditions, to produce oxygenated products comprising alcohols and, optionally, aldehydes; and working up the oxygenated products to recover therefrom a primary alcohol as a biodegradable surfactant precursor.

* * * * *

UNITED STATES PATENT AND TRADEMARK OFFICE
CERTIFICATE OF CORRECTION

PATENT NO.      : 6,756,411 B2
DATED           : June 29, 2004
INVENTOR(S)     : Mark Justin Betts et al.

It is certified that error appears in the above-identified patent and that said Letters Patent is hereby corrected as shown below:

<u>Title page,</u>
Item [30], Foreign Application Priority Data, "28, 1996" should read -- 29, 1995 --.

Signed and Sealed this

Seventeenth Day of August, 2004

JON W. DUDAS
*Acting Director of the United States Patent and Trademark Office*